United States Patent [19]

Panster et al.

[11] Patent Number: 4,645,847

[45] Date of Patent: Feb. 24, 1987

[54] PHENYLENE GROUP-CONTAINING ORGANOPOLYSILOXANES MODIFIED WITH FUNCTIONAL GROUPS AND METHOD OF THEIR PREPARATION

[75] Inventors: Peter Panster, Rodenbach; Peter Kleinschmit, Hanau, both of Fed. Rep. of Germany

[73] Assignee: Degussa Aktiengesellschaft, Frankfurt, Fed. Rep. of Germany

[21] Appl. No.: 865,487

[22] Filed: May 21, 1986

[30] Foreign Application Priority Data

May 25, 1985 [DE] Fed. Rep. of Germany ....... 3518880

[51] Int. Cl.$^4$ ............................. C07F 7/08; C07F 7/00; C07F 7/28; C07F 5/06
[52] U.S. Cl. ............................................ 556/9; 556/10; 556/405; 556/434; 528/9; 528/16; 528/17; 528/33; 528/34
[58] Field of Search .................... 556/434, 405, 9, 10; 528/9, 16, 17, 33, 34

[56] References Cited

U.S. PATENT DOCUMENTS

| | | | |
|---|---|---|---|
| 3,209,018 | 9/1965 | Merker | 556/434 X |
| 3,304,320 | 2/1967 | Spencer | 556/434 X |
| 4,442,040 | 4/1984 | Panster et al. | 556/10 X |

Primary Examiner—Paul F. Shaver
Attorney, Agent, or Firm—Beveridge, DeGrandi & Weilacher

[57] ABSTRACT

Functionalized phenylene group-containing organopolysiloxanes, comprising a plurality of identical or different units of the formula:

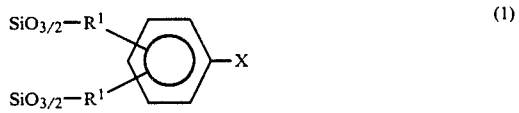

(1)

where in each case all three possible isomers in relation to the position of the $SiO_{3/2}$—$R^1$ substituents on the phenylene group can be present concurrently, in which the bridge groups $R^1$ represent the groups —$CH_2$—$CH_2$— or $CH_3$—CH<, X represents Cl, Br, $CH_2Cl$, $P(C_6H_5)_2$, and $CH_2P(C_6H_5)_2$, and the free valences of the oxygen atoms are saturated by silicon atoms of other groups of formula (1) and/or by cross-linking agents. Also disclosed is a process for the preparation of said polysiloxanes.

9 Claims, No Drawings

PHENYLENE GROUP-CONTAINING ORGANOPOLYSILOXANES MODIFIED WITH FUNCTIONAL GROUPS AND METHOD OF THEIR PREPARATION

The invention has as its object new phenylene group-containing organopolysiloxanes, which can be used as extremely effective carriers of active substances by appropriate modification with a variety of functional groups. These new carriers possess a high capacity for functionalization as well as the excellent properties of inorganic carrier materials.

Another object of the invention is to provide a process for preparing these functionalized organopolysiloxanes. Processes for the preparation of their monomeric precursors as well as the monomer precursors themselves also will be described.

Active substances or functional groups bound to an insoluble carrier by chemical bonds, have the advantages of easy separability, recyclability, and recoverability of the active components in industrial applications compared to active substances or functional groups employed in the homogeneous phase. In addition, the stability and residence time of an agent modified according to this principle can often be markedly increased and its selectivity desirably influenced. Whereas ion exchangers, for example, are almost classic examples of this concept, enzymes or complex metal catalysts fixed on a carrier, for example, have been the subject of recent investigations and synthesis attempts.

Heretofore, organic polymers, especially polystyrene, have mainly been used as carriers for this purpose. Examples thereof are described, for instance, in British Pat. No. 1,277,736 or in U.S. Pat. No. 3,708,462. Although inorganic polymeric systems such as silicic acid or silica gel, for example, have various advantages, they are generally less suitable for this application, since they can be modified by the introduction of functional groups only to a limited extent and the functional unit can be cleaved rather easily via hydrolytic means. In the absence of truly suitable carrier systems, attempts have been made to anchor phenylsiloxanes on silica gel (cf. J. Conan, M. Batholin, and A. Guyet, J. Mol. Catal. 1, 375, 1975/76). In principle, however, such systems have the same disadvantages as pure inorganic carriers themselves.

Therefore, the present invention has as its object the provision of carrier systems that combine both the advantages of the organic and the inorganic carrier materials; i.e., they possess a fixed, rigid structure and high temperature stability and resistance to aging, they swell to a limited extent only, or not all, and are insoluble in organic solvents, and they have a high capacity for active substances or functional groups, which are readily accessible and can be securely anchored to the polymeric skeleton.

This object was achieved with new phenylene group-containing organopolysiloxanes, which are disclosed in relation to material and preparation in the parallel application corresponding to U.S. application Ser. No. 865,486, filed concurrently herewith, the entire disclosure of which is relied on and incorporated by reference. They are accessible according to current concepts of organic synthesis either from the above-mentioned polysiloxanes or from the corresponding initial monomeric products. This functionalized phenylene group-containing organopolysiloxanes are characterized by the fact that they contain a plurality of units represented by the formula:

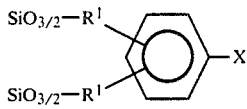
(1)

where in each case all three possible isomers, in relation to the position of the $SiO_{3/2}$—$R^1$ substituents on the phenylene group, can be present concurrently, in which the bridge groups $R^1$ represent the groups —$CH_2$—$CH_2$— or $CH_3$—$CH<$ and can be identical or different, and X represents Cl, Br, $CH_2Cl$, $P(C_6H_5)_2$, and $CH_2P(C_6H_5)_2$, and the free valences of the oxygen atoms are saturated by silicon atoms of identical or different groups of formula (1) and/or by cross-linking bridge groups:

or

or

or

or

or

or

or

or

or

or

in which R' is a methyl or ethyl group, and/or a phenylene unit represented by formula:

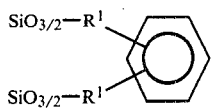

(2)

in which the bridge groups $R^1$ have the same meaning as in formula (1) and can be identical or different, and the ratio of the sum of the Si atoms of formulas (1) and (2) to the bridge atoms silicon, titanium, zirconium, and aluminum can be 1:0 to 1:15.

The ratio of the X-substituent carrying phenylene units of formula (1) to the Si-, Ti-, Zr-, and Al-containing cross-linking groups optionally provided in the polymeric structure and the phenylene groups of formula (2) has a lower limit determined by the fact that a minimum concentration of 0.01 meq of X groups per gram of organopolysiloxane is present, and a maximum concentration is present if no unsubstituted phenylene groups of formula (2) and no cross-linking Si-, Ti-, Zr-, and Al-containing bridge groups are present in the solid matter. However, it is to be noted that this situation is not necessarily present, because depending on the use of these polymers modified by incorporation of substituent-X of formula (1), it may be advantageous, for example, for the purpose of controlling the density of X groups or for setting certain specific surfaces or surface properties, etc., if the cross-linking bridge groups of the above-mentioned type, or also groups of formula (2), are present in the solid matter. Thus, for example, it may be of advantage that the solid polymer have in the majority of cases units of formula (1) only on the surface, so that no diffusion problems with arise for the other reactants in subsequent reactions or in direct applications for end purposes.

Another object of the invention is to provide a process for the preparation of organopolysiloxanes containing phenylene groups of formula (1) modified with functional groups. The process comprises reacting a phenylene group-containing organopolysiloxane, having a plurality of identical or different units of the general formula:

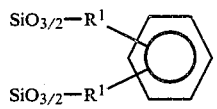

(2)

where in each case all three possible isomers, in relation to the position of the $SiO_{3/2}$—$R^1$ substituents on the phenylene group, can be present concurrently, wherein the bridge groups $R^1$ represent the groups —$CH_2$—$CH_2$— or $CH_3$—CH< and can be identical or different, and the free valences of the oxygen atoms are saturated by silicon atoms of other groups of formula (2) and/or by cross-linking bridge groups:

$SiO_{4/2}$ or $R'SiO_{3/2}$ or $R_2'SiO_{2/2}$ or $TiO_{4/2}$ or $R'TiO_{3/2}$ or $R_2'TiO_{2/2}$ or $ZrO_{4/2}$ or $R'ZrO_{3/2}$ or $R_2'ZrO_{2/2}$ or $AlO_{3/2}$ or $R'AlO_{2/2}$ in which R' is a methyl or ethyl group, and the ratio of the sum of the Si atoms in formula (2) to the bridge atoms silicon, titanium, zirconium, and aluminum can be 1:0 to 1:15, with stoichiometric, reduced or excess amounts of a partially or totally dissolved gaseous, liquid, or solid reagent containing at least one functional group X, known for the substitution of at least one hydrogen atom on the ring by the functional substituent X necessary or desired for a specific end use or application, in a solvent at temperatures of −80° C. to 200° C. at standard or gage pressure corresponding to the sum of the partial pressures at the specific temperature, for a period of a few minutes to several days at temperatures of from −78° C. to 200° C., said reaction process, if necessary, being repeated with a change of solvent, the solid being then separated from the liquid phase by any suitable technique or the solvent is removed by distillation, optionally washing the modified solid with another solvent, then optionally drying the solid under a protective atmosphere or in vacuum at a temperature up to 200° C., then optionally tempering for 1 hour to 5 days at temperatures of from 100°–400° C. in air or under a protective gas at standard pressure, in vacuum or at gage pressure, then grinding and/or classifying, where necessary, whereby some of these steps can be omitted or carried out in a different order of sequence.

The phenylene group-containing organopolysiloxanes of formula (2) employed as starting material can be obtained by hydrolyzing and polycondensing a silane represented by the formula:

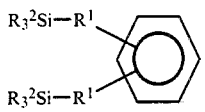

in which the bridge groups $R^1$ represent the groups $-CH_2-CH_2-$ or $CH_3-CH<$ and can be identical or different, and the substituents $R^2$ represent a linear or branched alkoxy group having 1 to 3 carbon atoms, or chloride and can be identical or different, optionally after the addition of a solvent and/or cross-linking agent precursor of the general formula:

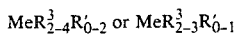

in which
Me=Si, Ti, Zr, or Al,
$R^3$ represents a linear or branched alkoxy group having 1 to 5 carbon atoms or chloride and
$R'$ is a methyl or ethyl group,
with stoichiometric or excess amounts of water,
optionally separating the product from the liquid phase after the addition of another solvent, optionally drying under a protective atmosphere or in vacuum at a temperature up to 200° C., then optionally tempering for 1 hour to 5 days at temperatures of 100° to 400° in air or under a protective gas, at standard pressure, in vacuum or at gage pressure, and grinding and classifying, where necessary.

Advantageously, with a view to the stability of the new phenylene group-containing organopolysiloxanes to partial and total solution at an increased temperature in water or aggressive polar organic solvents, the product, after preparation, is exposed to said tempering, optionally coupled with drying, or also shortly before use. The technique of tempering is known from the synthesis of inorganic polymers such as, for example, silicic acids or silica gels. It causes further dehydration upon reaction of neighboring silanol groups or cleavage of alkoxy groups still present in the polymer substance or Si-bound chlorine atoms in the form of the corresponding alcohol or hydrogen chloride with concurrent formation of siloxane bonds.

In principle, $R^2$ represents other substituents such as, for example, Br, I, $OC_6H_5$ or $OC_2H_4OCH_3$, yet the use thereof offers no advantages, but rather disadvantages, for example, with respect to the accessibility of the corresponding silanes or in regard to the hydrolysis rate and the by-products formed during hydrolysis. Occassionally, in part as a function of the type of solubilizer employed and if $R^2$ represents a linear or branched alkoxy group, it can be advantageous to add a small amount of a typical polycondensation catalyst, in the simplest case in aqueous HCl solution, to the silane to be polycondensed. From this point of view, the hydrolysis rate is understandably highest when $R^2$ represents chloride.

Although the hydrolysis and polycondensation can be carried out without a solubilizer, the employment thereof is generally preferable for practical reasons.

The selection of the solvents for the introduction of substituent X focuses primarily on the reagents with which the organopolysiloxanes of formula (2) employed as the starting material are reacted. Because this involves current reaction principles of organic synthesis, known from textbooks, these solvents are generally the same as those used in the corresponding reactions with monomers. Therefore, they need not be explained further.

When reacting solids with dissolved, solid or gaseous reactants, it is generally advantageous, for reasons of the most preferred diffusion, that the particular solid material be relatively finely dispersed. Thus, it is possible to grind the solid before or during the treatment with the functional agent. In view of certain applications of the functionalized phenylene group-containing polysiloxanes; i.e., in a fixed bed reactor, it can be advantageous to leave the solid material as coarsely grained as possible. In this case, according to one modification of the present invention, for example, only the surface area of a solid particle of the organopolysiloxane of formula (2) is chemically modified in the manner indicated. This can be achieved, for example, by using less than stoichiometric amounts of the functionalization agent or by short reaction times.

Suitable functionalization agents for purposes of the invention by which modifications is achieved by introduction of functional groups into polymers, consisting of units of formula (2), are in particular elemental chlorine or bromine, chloromethyl methyl ether or chloromethyl ethyl ether, formaldehyde, paraformaldehyde, the methyl acetal or ethyl acetal of formaldehyde, plus hydrogen chloride, and lithium, sodium or potassium diphenylphosphide. Thus, the chlorination or bromination of these polymers can occur by reaction with chlorine or bromine in a solvent such as carbon tetrachloride in the presence of iron powder or iron(III) chloride or other Lewis acids (see, for example, G. B. Bachman et al., J. Org. Chem. 12, 108, 1947). The chloromethylation can be carried out with the aid of chloromethyl methyl ether or chloromethyl ethyl ether in the presence of anhydrous tin tetrachloride in chloroform or by reaction with formaldehyde or modification thereof and hydrogen chloride gas (see, for example, R. B. Merrifield, J. Am. Chem. Soc. 85, 2149, 1963). The introduction of the diphenylphosphine group into the previously halogenated or chloromethylated polymer can be carried out, for example, as described by K. G. Allum et al. in J. Organomet, Chem. 87, 189 (1975). The reaction conditions and parameters for introduction of functional groups in thus known in the art.

In order to largely exclude any conceivable secondary reactions on the polysiloxane matrix for the abovementioned modification, it can be advantageous to previously subject the solid of formula (2) to be modified to a tempering treatment of the type described earlier. Alternatively, a similar effect, i.e., complete reaction of still existing silanol groups, can also be achieved, for example, by reaction with $ClSi(CH_3)_3$, as described, for example, in J. Organomet. Chem. 87, 189 (1975).

As an alternative to the previously described process for the preparation of polysiloxanes containing the functionalized units of formula (1), the monomeric silanes of formula (3) can in principle also be functionalized in the manner indicated above. Although this is certainly feasible with some types of reaction, the functionalization of polymers with units of formula (2) is generally preferred, especially because of the additional reactivity of the alkoxysilyl and/or chlorosilyl groups indicated in these cases.

The organopolysiloxanes of the invention have specific surfaces areas of less than 1 m²/g to 1000 m²/g depending on the starting material, polycondensation medium employed, and polycondensation conditions. The particle sizes of the solid product can be adjusted within certain ranges and vary from about 0.1 micron to 1 cm.

The invention will now be further described with reference to the following illustrative embodiments.

EXAMPLE 1

100 g of an isomeric compound comprising up to about 90% by weight of the ortho-, meta-, para-isomer mixture (12% by weight/65% by weight/23% by weight) of the chlorosilane;

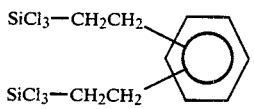

and up to about 10% of the chlorosilanes

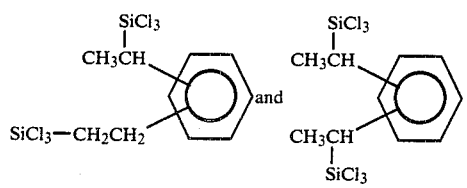

with the same isomeric distribution was dissolved in about 100 ml of toluene. The solution was combined with 100 g of desalinated water over a 30-minute period in a 1-liter three-neck flask with KPG stirrer and reflux condenser with vigorous stirring. Spontaneous thickening occurred with considerable foaming immediately after addition of 30 ml of $H_2O$, so that the flask contact could no longer be stirred within a short time. After addition of another 50 ml of toluene and 50 ml of water, the mixture was heated to reflux temperature and stirred for 2 hours. The mixture was then cooled and the resulting white solid was filtered through a suction filter, and washed initially with 100 ml of ethanol, then with 3 liters of water until it was almost free of HCl. After 12 hours of drying at 150° C./100 mbar and 30 hours of tempering at 250° C. under an $N_2$ atmosphere, these was obtained in the form of a white powder, 58.8 g (99.8% of the theoretical) of the desired phenylene group-containing organopolysilane, comprising up to about 90% of units of the formula:

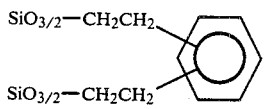

and up to about 10% of units of the formula:

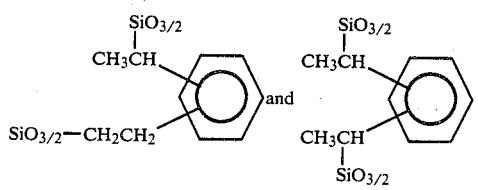

(corresponding to the distribution of amounts by weight determined for the starting material)

| Elemental analyses: | % C | % H | % Si | % Cl |
|---|---|---|---|---|
| Theoretical: | 50.81 | 5.12 | 23.76 | 0 |
| Found: | 48.95 | 5.33 | 22.47 | 0.02 |

After drying and tempering, the product was ground and classified. The 0.3–1.2 mm particle size fraction was used for the determination of the specific surface area by an area meter, which gave a value of 338 m²/g. A DSC analysis of the product under an $N_2$ atmosphere yielded at incipient endothermic decomposition of the polymer at over 280° C.

EXAMPLE 2

100 g of an isomeric compound comprising up to about 90% by weight of the ortho-, meta-, para-isomer mixture (12% by weight/65% by weight/23% by weight) of the ethoxysilane

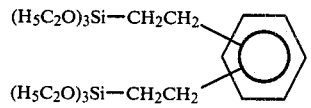

and up to about 10% of the ethoxysilanes:

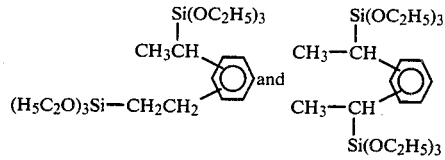

with the same isomeric distribution was mixed with 120 ml of ethanol. The mixture was heated in a 1-liter three-neck flask with a KPG stirrer, a reflux condenser, and dropping funnel to reflux temperature, and combined with 50 ml of $H_2O$ all at once with vigorous stirring.

Just a few minutes after the addition of water, the batch thickened and a voluminuous solid appeared. This was stirred for another 2 hours at reflux, and then filtered through a suction filter, and washed first with 100 ml of ethanol and then with 2 liters of $H_2O$. After 24 hours of drying at 150° C./100 mbar, 52.7 (102.3% of the theoretical) of the desired product was obtained in the form of a white solid. The composition of this organopolysiloxane corresponded to that of the product obtained in Example 1, both in regard to structure and in relation to the isomer distribution.

| Elemental analyses: | % C | % H | % Si |
|---|---|---|---|
| Theoretical: | 50.81 | 5.12 | 23.76 |
| Found: | 49.03 | 6.01 | 22.34 |

The 0.3–1.2 mm fraction of the classified product has a specific surface area of 89 m²/g (area meter).

EXAMPLE 3

75 g of the starting material used in Example 2 and 68.12 g of $Si(OC_2H_5)_4$ were combined in 100 ml of ethanol. The mixture was heated in a 1-liter three-neck flask with a KPG stirrer, a reflux condenser, and dropping funnel to reflux temperature. 50 g of water was added all at once with vigorous stirring. The flask content gelled immediately after the water was added. The flask content was stirred for another hour at reflux, then cooled, filtered off, and washed with 300 ml of ethanol. After 10 hours of drying at 150° C. and 2 hours of tempering at 300° C. under an $N_2$ atmosphere, 58.9 g (101.0% of the theoretical) of a polymeric product, comprising up to about 90% of units of the formula:

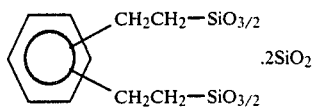

and up to about 10% of units of the formula:

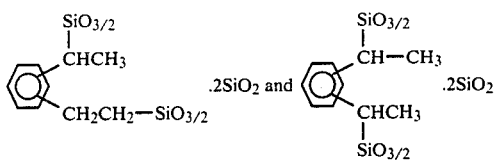

(corresponding to the distribution of amounts by weight determined for the starting material) with an ortho-/meta-/para-isomer ratio of 12% by weight/65% by weight/23% by weight was obtained.

| Elemental analyses: | % C | % H | % Si |
| --- | --- | --- | --- |
| Theoretical: | 33.69 | 3.39 | 31.51 |
| Found: | 32.21 | 3.56 | 30.87 |

EXAMPLE 4

20 g of the phenylene group-containing organopolysiloxane prepared in Example 1 with an adjusted particle size of 0.1–0.2 mm was combined together with 150 mg of iron powder in 75 ml of chloroform. To this suspension in a 250 ml three-neck flask with KPG stirrer, reflux condenser and dropping funnel was added dropwise 14.87 g of bromine, dissolved in 20 ml of chloroform, over a 15 minute period at room temperature with vigorous stirring. Then, the suspension was heated to reflux temperature over a 1 hour period. The mixture was stirred for another 3 hours at this temperature, then cooled and the solid was filtered off. This was washed first with 100 ml of $CHCl_3$ and then with 100 ml of ethanol. After 14 hours of drying at 120° C./100 mbar, 24.5 g of the desired product with a bromine content of 20.33% was obtained. A bromine content of 25.34% was expected for total simple bromination of all phenylene groups present in the solid.

EXAMPLE 5

10 g of the phenylene group-containing organopolysiloxane prepared in Example 1 with an adjusted particle size of 0.3–1.2 mm was combined together with 100 mg of anhydrous iron(III) chloride in 75 ml of $CCl_4$. Elemental chloride was passed through this suspension in a 250 ml three-neck flask with a brine reflux condenser (−20° C.), KPG stirrer, and gas inlet tube at room temperature over a 4 hour period with vigorous stirring. Then, the solid was filtered off, washed with 200 ml of $CCl_4$, and dried for 15 hours at 120° C./100 mbar. 10.3 g of the desired product with a chlorine content of 6.50% was obtained. This corresponds to an approximately 50% monochlorination of all phenylene groups present in the polysiloxane.

EXAMPLE 6

20 g of the phenylene group-containing organopolysiloxane prepared in Example 2 and 100 ml of petroleum ether (80°–110° C.) were combined in a 500 ml three-neck flask with a KPG stirrer, reflux condenser, and dropping funnel. At a temperature of 35°–40° C., a mixture of 25 ml of chlorodimethyl ether and 2.5 ml of $SnCl_4$ was added dropwise to this suspension over a 30 minute period. Then, the mixture was stirred for another 4 hours at this temperature, then 200 ml of ice water was added to the reaction suspension. After another 0.5 hours of stirring, the mixture was filtered off, the solid was washed with 150 ml of methanol, and dried for 10 hours at 130° C./100 mbar. The weighted product (20.3 g) had a chlorine content of 4.0%, which corresponds to an approximately 30% chloromethylation of all phenylene groups present.

EXAMPLE 7

20 g of the $SiO_2$ cross-linked phenylene group-containing organopolysiloxane prepared in Example 3 was suspended in 100 g of concentrated hydrochloric acid. 10 g of 40% formalin solution was added dropwise initially at 50° C. over a 1 hour period to this suspension in a 500 ml three-neck flask with a KPG stirrer, reflux condenser, and dropping funnel and/or gas inlet tube. Then, the suspension was stirred for another 5 hours at 50° C., during which the hydrogen chloride gas was fed in through the gas inlet tube. After this time period, the material was filtered off, the remaining solid was washed with 300 ml of desalinated water, and then dried for 24 hours at 130° C./100 mbar. The weighed product has a chlorine content of 4.8% which corresponded to an approximately 50% chloromethylation of all phenylene groups present.

EXAMPLE 8

9 g of the brominated phenylene group-containing organopolysiloxane prepared in Example 4 was suspended in 40 ml of n-hexane. The suspension was cooled to −25° C. in a cooling bath. To this suspension was added dropwise 17.2 ml of a 1.6 molar lithium butyl solution in n-hexane with vigorous stirring. Next the mixture was stirred for another 6 hours at this temperature, then the solvent was drawn out of the flask and fresh n-hexane cooled to −25° C. was added. Then, 5.1 ml of $ClP(C_6H_5)_2$, diluted with 5 ml of n-hexane, was added dropwise over a 10 minute period. The mixture was stirred for another 8 hours at room temperature, the solid material was then filtered off, washed with 30 ml of n-hexane and then with 100 ml of ethanol, and dried for 3 hours at 150° C./0.1 mbar. There was obtained 9.2 g of the desired product with a phosphorus content of 2.51%. This indicates that about 25% of all bromine atoms present are replaced by $P(C_6H_5)_2$ groups.

EXAMPLE 9

10.0 g of the chloromethylated phenylene group-containing organopolysiloxane prepared in Example 6 was suspended in 40 ml of dried tetrahydrofuran. This suspension was combined with 14.9 ml of a solution of $LiP(C_6H_5)_2$ in tetrahydrofuran (corresponds to 3.50 g of $LiP(C_6H_5)_2$) at room temperature with stirring, and then stirred for 6 hours at reflux. It was cooled, the solid was filtered off, washed with 50 ml of tetrahydrofuran and with 50 ml of ethanol, and dried for 3 hours at 150° C./0.1 mbar. The obtained 11.1 g of product had a P content of 1.5%, which corresponds to about 65% substitution of the chlorine atoms present by $P(C_6H_5)_2$ groups.

Further variations and modifications of the present invention will be apparent to those skilled in the art from a study of the foregoing and are intended to be encompassed by the claims appended hereto.

The German priority application No. P 35 18 880.4 is relied on and incorporated herein by reference.

We claim:

1. Phenylene group-containing organopolysiloxanes modified by incorporation of at least one functional group comprising a plurality of identical or different units represented by the formula:

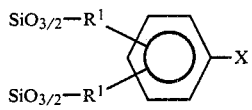 (1)

where in each case all three possible isomers in relation to the position of the $SiO_{3/2}$—$R^1$ substituents on the phenylene group can be present concurrently, in which the bridge groups $R^1$ represent the groups —$CH_2$—$CH_2$— or $CH_3$—CH<, and can be identical or different, X represents Cl, Br, $CH_2Cl$, $P(C_6H_5)_2$, $CH_2P(C_6H_5)_2$, and the free valences of the oxygen atoms are saturated by silicon atoms of other groups of

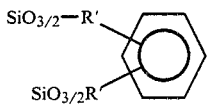

and/or by cross-linking bridge groups:

$SiO_{4/2}$ or $R'SiO_{3/2}$ or $R_2'SiO_{2/2}$ or $TiO_{4/2}$ or $R'TiO_{3/2}$ or $R_2'TiO_{2/2}$ or $ZrO_{4/2}$ or $R'ZrO_{3/2}$ or $R_2'ZrO_{2/2}$ or $AlO_{3/2}$ or $R'AlO_{2/2}$ in which R' is a methyl or ethyl group, and/or by phenylene units of the general formula (1), in which the bridge groups $R^1$ have the same meaning as in formula (2) and can be identical or different, and the ratio of the sum of Si atoms of the units in formulas (1) and (2) to the bridge atoms silicon, titanium, zirconium, and aluminum can be 1:0 to 1:15.

2. A process for the preparation of the compounds according to claim 1, comprising reacting a phenylene group-containing organopolysiloxane, which has a plurality of identical of different units represented by the formula:

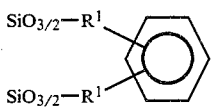 (2)

where in each case all three possible isomers, in relation to the position of the $SiO_{3/2}$—$R^1$ substituents on the phenylene group, can be present concurrently, in which the bridge groups $R^1$ represent the groups —$CH_2$—$CH_2$— or $CH_3$—CH< and can be identical or different, and the free valences of the oxygen atoms are saturated by silicon atoms of other groups of formula (2) and/or by cross-linking bridge groups:

$SiO_{4/2}$ or $R'SiO_{3/2}$ or $R_2'SiO_{2/2}$ or $TiO_{4/2}$ or $R'TiO_{3/2}$ or $R_2'TiO_{2/2}$ or $ZrO_{4/2}$ or $R'ZrO_{3/2}$ or $$R_2'ZrO_{2/2}$$

or $$AlO_{3/2}$$

or $$R'AlO_{2/2}$$

in which R' is a methyl or ethyl group, and the ratio of the sum of the Si atoms in formula (2) to the bridge atoms silicon, titanium, zirconium, and aluminum can be 1:0 to 1:15, with stoichiometric, reduced or excess amounts of a partially or totally dissolved, gaseous, liquid, or solid functional reagent containing the substituent X for the substitution of at least one hydrogen atom on the ring of said organopolysiloxane by the functional substituent X;

in a solvent at temperatures of −80° C. to 200° C. at standard or gage pressure corresponding to the sum of the partial pressures of the components of the reaction mixture at the specific temperature, for a period from a few minutes to several days at temperatures of −78° C. to 200° C., separating the solid from the liquid phase.

3. The process according to claim 2 wherein the solid is separated from the liquid phase by distilling the solvent.

4. The process according to claim 2 wherein the solid is washed with another solvent and dried.

5. The process according to claim 2 wherein the solid is dried under a protective atmosphere or in vacuum.

6. The process according to claim 5 wherein the drying is carried out at a temperature of up to 200° C.

7. The process according to claim 2 wherein the product is tempered for 1 hour to 5 days at a temperature of 100° to 400° C. in air or under a protective gas at standard pressure, in vacuum or at gage pressure.

8. The process according to claim 2 wherein the dry, solid product is subject to grinding to produce a finely divided product.

9. The process according to claim 2, wherein the functional reagent is selected from the group consisting of chlorine, bromine, chloromethyl methyl ether, chloromethyl ethyl ether, formaldehyde, the methyl acetal or ethyl acetal of formaldehyde, paraformaldehyde in each case in combination with hydrogen chloride; and lithium, sodium and potassium diphenylphosphide.

* * * * *